United States Patent [19]

Vandeputte et al.

[11] Patent Number: 5,750,118
[45] Date of Patent: May 12, 1998

[54] VACCINE METHOD AGAINST SWINE DYSENTERY

[75] Inventors: Joris Frans Vandeputte, Diemoz; Marc Jean Guillaud, Lyon; Francis William Milward, Tassin, all of France

[73] Assignee: Rhone Merieux, Lyon, France

[21] Appl. No.: 571,944

[22] PCT Filed: Jul. 8, 1994

[86] PCT No.: PCT/FR94/00850

§ 371 Date: Mar. 14, 1996

§ 102(e) Date: Mar. 14, 1996

[87] PCT Pub. No.: WO95/01805

PCT Pub. Date: Jan. 19, 1995

[30] Foreign Application Priority Data

Jul. 8, 1993 [FR] France .................... 93 08396

[51] Int. Cl.⁶ .................................................. A61K 39/02
[52] U.S. Cl. .................................. 424/262.1; 435/252.33; 435/252.1
[58] Field of Search ................ 424/262.1; 435/252.1, 435/252.33

[56] References Cited

U.S. PATENT DOCUMENTS 4,758,517  7/1988  Parizek ........................... 435/252.1
4,868,118  9/1989  Norgard ......................... 435/252.33

OTHER PUBLICATIONS

Clin, J. et al, J. cell Biochem Suppl o(17 part C) 1993, 54.

Pig Products and Research Highlights, Animal–Pharm, vol. 259, p. 16, 920901.

*Primary Examiner*—James C. Housel
*Assistant Examiner*—Ginny Allen Portner
*Attorney, Agent, or Firm*—Frommer Lawrence & Haug LLP; William S. Frommer; Thomas J. Kowalski

[57] ABSTRACT

A method for vaccination against haemorrhagic dysentery of pigs with a vaccine including an effective quantity of inactivated and adjuvant-containing *Serpulina hyodysenteriae* antigen which is administered intradermally, it being possible for the vaccine to be especially formulated in a dose volume of between about 0.1 and 0.3 ml, especially of the order of 0.2 ml. A vaccination kit for administration of the vaccine may include, for example a pressurized jet administering apparatus, designed for the intradermal administration of individual doses of vaccine and combined with a supply source containing a vaccine of this type.

13 Claims, No Drawings

VACCINE METHOD AGAINST SWINE DYSENTERY

The present invention relates to a vaccine against haemorrhagic dysentery of pigs (swine disentery) and to a vaccination kit using this vaccine as well as to a process for treating pigs against this disease.

The organism responsible for the haemorrhagic dysentery syndrome is *Serpulina hyodysenteriae* (formerly *Treponema hyodysenteriae*). 9 serotypes are currently recognized, identified mainly in the U.S.A., but also in Mexico, in England, in Denmark, in Holland, in Australia (Mapother and Joens classification, J. Clin. Microbiol. 1985, 22, 161–164) and recently in Canada for serotypes 8 and 9 (Z. Li. J. Clin. Microbiol. 1991, 29, 2794–2797; 1992, 30 (11), 2941–2947).

Numerous vaccination trials have been carried out until now. While it has been possible to demonstrate the feasibility of a vaccine through various trial models, few products have been exploited in the field because of lack of efficacy and problems of safety.

The vaccine options which have been the subject of previous research studies, or which are the subject of current research studies, cover the whole range of possibilities in respect of vaccines, namely:

vaccines with whole, inactivated or attenuated live bacteria, termed conventional vaccines, conventional or recombinant bacterial subunit vaccines.

U.S. Pat. No. 4,100,272 has thus proposed a killed cell vaccine for parenteral administration, which should result in partial or total immunizations via the systemic route. U.S. Pat. No. 4,152,413 has proposed an oral vaccine comprising enteric capsules containing killed cells for the liberation of active ingredients in the intestines; same approach in U.S. Pat. No. 4,152,414 and U.S. Pat. No. 4,203,968 where *S. hyodysenteriae* is combined with killed Bacteroides vulgatus or *Furobacterium necrophorium* cells. U.S. Pat. No. 4,152,415 proposes a parenteral administration of a killed cell vaccine followed by oral administration of a vaccine in enteric capsules. Patent U.S. Pat. No. 4,203,968 proposes a parenteral preparation containing killed *S. hyodysenteriae* cells and killed Bacteroides vulgatus cells and also proposes combining it with an oral formulation. U.S. Pat. No. 4,469,672 and U.S. Pat. No. 4,748,019 propose vaccinating by administering killed cells parenterally, and then orally. Patent Application EP-A-201,796 describes a process for culturing *S. hyodysenteriae* in a nutritive medium containing a cholesterol-rich bovine fraction for producing an inactivated vaccine formulated in the form of an emulsion with an adjuvant consisting of polyacrylic acid and polysaccharide in cross-linked form. According to this document, a resistance could be obtained after two intramuscular injections, whereas known vaccines require several intravenous injections. Finally, European Patent Application EP-A-339 040 proposes administering parenterally live cells and killed cells in the presence of oxygen.

None of these approaches have permitted the production of an effective vaccine.

The Taylor strain (1972), attenuated by 80 passages on horse blood agar, is also known whose efficacy was explored by oral vaccination at repeated doses of the order of $5\times10^9$ CFU at 9 weeks of age (Hudson, Br. Vet. J. 1974, 130, 37–40 and Res. Vet. Sci. 1976, 21, 366–367). This vaccine showed only a limited efficacy.

The so-called spontaneously attenuated VS1 strain, of Lysons of the British Technology Group (strain NCTC 11628) has also been used, and at repeated doses of $10^8$ CFU, in combination with 2 injections of an inactivated formulation, with oil adjuvant (strain P18A, NCTC 11615, dose of $5\times10^9$ CFU).

A solution currently recommended for producing an attenuated live vaccine is to delete from the bacterium its virulent factors, leaving the chromosome only with its functions for the survival of the bacterium (M. B. Koopman, Infect. Immun. 1992, 60, 2920–2925).

The failure of the conventional vaccine approach has recently been confirmed by J. P. TRONEL (Thesis, National Veterinary School of Lyon: "Contribution to the study and development of a vaccine against haemorrhagic dysentery of pigs", made public on 17 Feb. 1993). The inactivated vaccines tested exhibited the disadvantages of vaccines with inactivated whole bacteria, namely especially weak immunogenicity and inflammatory lesions at the point of injection. The author concludes that this type of vaccine is not capable of eliciting a sufficiently protective immune response, as is also the case for the only commercially available formulation (inactivated and adjuvant-containing whole bacteria vaccine) tested in parallel in the field.

Faced with the failure of the so-called conventional vaccine approaches, various teams focused on subunit vaccines and the recombinant approach. There may be mentioned for example International Patent Applications WO90/2565, WO90/15132, European Patent Applications EP-A-350 715, EP-A-282 965, EP-A-491 859, EP-A--502 100 and U.S. Pat. No. 5,176,910.

This also corresponds to the conclusions of J. P. Tronel (supra) who proposes, in addition "the combination of a systemic administration of the protective bacterial antigens, combined with the prior placing of the digestive mucous membranes into contact with the same antigens", a condition which is essential in this context.

The applicant has now discovered very surprisingly that it was possible to effectively vaccinate pigs against haemorrhagic dysentery using a conventional type vaccine under specific conditions, and this without safety problems.

The subject of the invention is therefore a vaccine against haemorrhagic dysentery of pigs, comprising an effective quantity of inactivated and adjuvant-containing *Serpulina hyodysenteriae* antigen (virulent or attenuated strain), for intradermal administration. Fractionated antigens or a mixture of fractionated antigens and whole antigens (non-fractionated intact bacterial bodies) can also be used. Fractionated antigens should especially be understood to mean the antigen fractions which are present in the antigen culture (see for example the experimental part) as well as the lysates of bacterial bodies, which are obtained for example by sonication.

Preferably, the dose volume is low, especially between about 0.1 and 0.3 ml and especially of the order of 0.2 ml.

The adjuvant may be advantageously an oil-type adjuvant, especially comprising a mixture of highly purified mineral oils and non-ionic surfactants, and the vaccine especially formulated in the form of a water-in-oil emulsion. Numerous mineral oil-based emulsions are nowadays known which are hydrocarbons obtained by refining petroleum. The surfactants serve, as is well known, to stabilize the emulsions and it is known that non-ionic hydrophilic surfactants are appropriate surfactants. Lipophilic surfactants with a very low HLB which also have an adjuvant power can also be used.

As oily phase, there may be mentioned for example a mixture of light liquid paraffin, ester of fatty acid and polyol and ester of ethoxylated fatty acid and polyol, for example in proportions of 500 to 700 mg, 10 to 100 mg and 1 to 33 mg respectively.

An aqueous-type adjuvant such as alumina gel can also be used.

Preferably, the vaccine according to the invention comprises an antigen of serotype 1, referenced 27 164 at the American Type Culture Collection.

In the case where a vaccination against various serotypes might be useful, the vaccine according to the invention may comprise a mixture of antigens of the various known serotypes encountered in the geographical region for which the vaccine is intended. A cross-protection between various serotypes makes it possible to resort to a single antigen or to an appropriate mixture of antigens.

Preferably, the vaccine comprises about $10^7$ to $10^9$ CFU equivalents of an antigen or appropriate mixture of antigens per dose, especially about $10^8$ CFU equivalents.

The present invention also relates to the use of inactivated *Serpulina hyodysenteriae* antigen for the preparation of a vaccine to be administered intradermally.

The subject of the invention is also a method of vaccinating pigs against swine dysentery, in which a preparation of inactivated and adjuvant-containing *Serpulina hyodysenteriae* antigen is administered intradermally to the pigs. In this method, an antigen preparation chosen from the group consisting of: whole antigens, fractionated antigens and mixtures thereof, is preferably administered. Preferably, an antigen preparation is administered in a dose volume of about 0.1 to 0.3 ml, especially about 0.2 ml.

According to one embodiment of the method of treatment, the invention covers a conventional vaccinal approach in which the animals are vaccinated under the conditions of the invention by one or more injections, especially two, for example at about 6 weeks, followed by a booster at about 9 weeks.

According to another embodiment of the method for treating pigs against haemorrhagic dysentery, the vaccine according to the invention is administered, under the conditions of the invention, to adult pigs shortly before the so-called "end of fattening" period (which may be for example of the order of one month in relation to the slaughtering of the animal). This approach shows good protection against the haemorrhagic dysentery syndrome in terms of weight loss and delay in marketing the animals during this period when the covering antibiotic treatments, which had to be stopped, can no longer cover infection by this germ. For example, the vaccine of the invention can be administered between for example 2 and 5 weeks before the beginning of this period, preferably about 2 weeks before. The vaccination may comprise especially one to two injections. In this latter case, it is the second injection which is considered in relation to the vaccination timetable which has just been defined. It will for example be possible for the two injections to follow each other at an interval or 2 weeks or more.

It will be understood that, in both cases, it will be possible for the vaccination conditions to vary with the breeding methods, which vary from one country to another and within the same country.

The subject of the invention is also a vaccination kit comprising a means of administration designed for the intradermal administration of individual doses of vaccine and combined with a supply source containing a vaccine as described above.

Preferably, the administration means is a pressurized jet administering apparatus, it being possible for the latter to produce a single jet or simultaneously several jets under pressure. An appropriate apparatus is for example the pressurized jet administering apparatus described in European Patent Application EP-A-420 744. Any other appropriate means, such as a syringe, can of course be used.

The invention will now be described in greater detail with the aid of a mode of preparation of a vaccine in accordance with the invention and a vaccination trial, which are given solely by way of example.

1) METHOD OF PREPARING THE ANTIGEN

The vaccinal antigen is prepared from the strain "*Treponema hyodysenteriae*, No. 27164, ATCC" cultured in soya bean trypticase (ST) medium enriched with pig serum, under strict anaerobic conditions. At the growth optimum, the culture is stopped and then inactivated by the addition of a merthiolate solution (at 1/1000 v/v final).

The inactivated culture is then washed and concentrated by centrifugation. The vaccinal antigen is thus a suspension of bacterial body and fractions thereof (bacterial wall, membrane, haemolysin, toxin), which is inactivated, washed in PBS, concentrated and stored at 4° C. Calculation of the culture titre before treatment makes it possible to know the equivalent final concentration of germs (CFU) of the antigen prepared.

The vaccine is formulated with a dilution of a vaccinal antigen which makes it possible to deliver the equivalent of $10^9$ CFU per dose, emulsified with an oily adjuvant (oil outer phase), the final volume of antigen representing ¼th of the volume of the injected dose.

2) VACCINATION TRIAL

The vaccine in accordance with the invention is administered intradermally (ID) to weaned SPF piglets at four weeks and six weeks of age (injection of booster the day before the challenge). One group of pigs is vaccinated intramuscularly (IM) (indicated route of administration, dose volume=5 ml) with commercial vaccine (inactivated and adjuvant-containing whole bacteria vaccine) under the same timetable conditions. The pigs intended for the control groups receive nothing. Another group of pigs is vaccinated intramuscularly (IM) with the vaccine in accordance with the invention.

The pigs are challenged (except a group of 5 control pigs for the maintenance conditions) via the intragastric route, on two consecutive days, with inocula titrating $10^9$ CFU, two weeks after the first vaccinal injection; the pigs are then six weeks old.

The clinical monitoring of the pigs after challenge is carried out on the basis of a daily record of individual clinical scores, and weighings at intervals of 7 days (4 weighings after challenge).

The experimental results are the following:
Growth of the pigs

| Groups | D (vacc.) | D (Ch.) | D7 | D14 | D21 | D28 |
|---|---|---|---|---|---|---|
| Controls | 7.5* | 11.6 | 12.6 | 13.2 | 14.7 | 18.9 |
| Challenged C. | 7.3 | 11.1 | 12.1 | 12.4 | 11.4 | 12.8 |
| Commercial vaccine | 7.1 | 10.6 | 10.9 | 12.1 | 10.8 | 13.2 |
| Vaccine of the invention IM | 7.3 | 10.8 | 11.2 | 13.2 | 15.1 | 18.0 |
| Vaccine of the invention ID | 7.6 | 11.0 | 11.6 | 13.3 | 13.9 | 17.0 |

\* = mean weight in the pig group, 5 in number, mean in kg.
(The difference in weight observed between the controls and those vaccinated IM and ID according to the invention is not significant)

Mean cumulative clinical scores

| Groups | D0–D7 | D8–D14 | D15–D21 | D22–D28 |
|---|---|---|---|---|
| Controls | 3 | 3 | 3 | 3 |
| Challenged C. | 3.36 | 5.96 | 7.64 | 8.68 |
| Commercial vaccine | 3.84 | 6.64 | 9.60 | 9.00 |
| Vaccine of the invention IM | 3.68 | 5.64 | 5.96 | 6.76 |
| Vaccine of the invention ID | 3.08 | 3.88 | 4.44 | 4.76 |

The threshold for the clinical score for the haemorrhagic dysentery syndrome=5

The scores indicated are cumulative daily mean scores over the period considered, on the basis of the following marks:

Consistency of stools

| |
|---|
| Normal, solid = 1 |
| Soft = 2 |
| Very soft, loose = 3 |
| Diarrhoeic, aqueous = 4 |

Composition of stools

| |
|---|
| Normal = 1 |
| Traces of mucus = 2 |
| Traces of blood = 3 |
| Haemorrhagic = 4 |

General state of the animal

| |
|---|
| Normal = 1 |
| Weakness = 2 |
| Marked loss of weight = 3 |
| Moribund = 4 |

Each criterion is noted daily, the individual score being the sum of the three marks. A mean of these marks is calculated from the range of measurements performed (35 measurements, 5 pigs over 7 days) for the group considered, over the period of observation (here 7 days) which is called "mean cumulative score".

Serological/kinetic responses

| Groups | D (vacc.) | D (Ch.) | D7 | D28 |
|---|---|---|---|---|
| Controls | 0.273* | 0.420 | 0.617 | 0.717 |
|  | 0.070** | 0.099 | 0.081 | 0.077 |
| Challenged C. | 0.293 | 0.448 | 0.821 | 1.321 |
|  | 0.067 | 0.099 | 0.252 | 0.237 |
| Vaccine of the invention ID | 0.284 | 1.508 | 1.753 | 1.772 |
|  | 0.064 | 0.072 | 0.045 | 0.059 |

* = mean of the OD values read for the group considered
** = standard error of the mean (no data For the commercial vaccine and the vaccine of the invention administered via the IM route)

These results demonstrate the protective affect of the vaccinal approach according to the invention in the experimental model:

the pigs vaccinated via the ID and IM routes with the antigen according to the invention maintain normal growth compared with the control group, whereas the animals vaccinated with the commercial vaccine have a behaviour which is identical to that of the animals in the challenged control group.

The clinical scores show that the group vaccinated via the ID route with the antigen in accordance with the invention does not express haemorrhagic dysentery syndrome (score<5), which is the case, on the other hand, for the animals in the challenged control group and the group with pigs vaccinated with the commercial vaccine or with the vaccine of the invention via the IM route.

The serological responses show a very good seroconversion from 14 days after the primary injection with the ID vaccine in accordance with the invention.

The vaccination of pigs intramuscularly is found to pose problems of safety at the point of injection. Nothing of the sort is observed in pigs vaccinated intradermally In conclusion, the vaccine according to the invention, administered intradermally, makes it possible to obtain protection against the disease and maintenance of growth, without inducing problems of safety.

We claim:

1. Method of vaccinating pigs against haemorrhagic dysentery, in which a preparation comprising inactivated Serpulina hyodysenteriae antigen and an adjuvant is administered intradermally to the pig.

2. Method according to claim 1, in which an antigen preparation chosen from the group consisting of:

whole antigens fractionated antigens, and mixtures thereof, is administered.

3. Method according to claim 1, in which the preparation is administered in a dose volume of about 0.1 to 0.3 ml.

4. Method according to claim 1, in which a first dose is administered at about 6 weeks, and a second booster dose is administered at about 9 weeks.

5. Method according to claim 1, in which the vaccine is administered to adult pigs before the end of the fattening period.

6. Method according to claim 1, wherein the adjuvant is an oily adjuvant.

7. Method according to claim 6, wherein the preparation is in the form of a water-in-oil emulsion.

8. Method according to claim 6, wherein the oily adjuvant comprises a mixture of highly purified mineral oils and non-ionic surfactants.

9. Method according to claim 1, wherein the adjuvant is alumina gel.

10. Method according to claim 1, wherein the antigen comprises an antigen of serotype 1, referenced "Treponema hyodysenteriae, No. 27164" at the American Type Culture Collection.

11. Method according to claim 3, wherein the dose volume is about 0.2 ml.

12. Method according to claim 3, wherein the preparation comprises $10^7$ to $10^9$ CFU equivalents of antigen per dose.

13. Method according to claim 12, wherein the preparation comprises $10^8$ CFU equivalents of antigen per dose.

* * * * *